United States Patent [19]

Pfister

[11] 4,250,097

[45] Feb. 10, 1981

[54] COMPOSITIONS FOR AND A METHOD OF PREVENTING DIABETIC COMPLICATIONS

[75] Inventor: Jurg R. Pfister, Los Altos, Calif.

[73] Assignee: Syntex (U.S.A.) Inc., Palo Alto, Calif.

[21] Appl. No.: 884,456

[22] Filed: Mar. 8, 1978

[51] Int. Cl.² .......................................... C07D 311/86
[52] U.S. Cl. .................................................. 260/335
[58] Field of Search ......................................... 260/335

[56] References Cited

U.S. PATENT DOCUMENTS

| | | | |
|---|---|---|---|
| 3,801,598 | 4/1974 | Pfister et al. | 260/335 |
| 3,803,174 | 4/1974 | Pfister et al. | 260/335 |
| 3,849,565 | 11/1974 | Pfister et al. | 424/283 |
| 3,859,286 | 1/1975 | Fleming et al. | 260/335 |
| 3,859,307 | 1/1975 | Carr et al. | 260/335 |
| 3,894,049 | 7/1975 | Pfister et al. | 260/335 |
| 4,078,078 | 3/1978 | Barnes et al. | 260/335 |

Primary Examiner—Norma S. Milestone
Attorney, Agent, or Firm—Tom M. Moran; Alan M. Krubiner; Gerard A. Blaufarb

[57] ABSTRACT

Compositions containing and methods of employing as the essential ingredients substituted xanthone carboxylic acid compounds which are useful in the prevention of complications of diabetes. Methods for preparing these compounds and the compositions and intermediates therein are also disclosed.

1 Claim, 3 Drawing Figures

FIG_1

FIG_2

COMPOSITIONS FOR AND A METHOD OF PREVENTING DIABETIC COMPLICATIONS

The present invention is directed to novel substituted xanthone carboxylic acid compounds and the compositions containing and methods for utilizing substituted xanthone carboxylic acid compounds as an essential ingredient in the treatment of symptoms associated with complications of diabetes mellitus.

It has been established that high levels of hexose sugars such as glucose, galactose and the like lead to the accumulation of various polyols in certain tissues, particularly the lens of the eye. As a result of these elevated levels of polyols, it is known that cataract formation results with a concomitant loss of lens clarity. The enzyme aldose reductase has been implicated in the formation of such cataracts in diabetes and galactosemia. See R. Van Heyninger, Nature, London, 184, 194 (1959). Aldose reductase is also suspected to be involved in some of the complications of diabetes such as nephropathy, neuropathy and retinopathy. The enzyme is known to convert aldose sugars to their corresponding sugar alcohols, i.e., aldose reductase converts glucose to sorbitol, xylose to xylitol, and galactose to dulcitol. The accumulation of these sugar alcohols eventually leads to development of cataracts, since there is no method for the body to remove the accumulated sugar alcohols, e.g., phosphorylation or related mechanisms. Accordingly, compounds that share the property of inhibition of aldose reductase activity are desirable therapeutic agents for the treatment of diabetic complications such as nephropathy, cataracts, neuropathy and retinopathy.

It has been established that a variety of flavonoids are effective inhibitors of lens aldose reductase. As shown by in vitro studies, quercetin, quercetrin and myrecetrin are among the most potent of these compounds.

U.S. Pat. No. 3,821,383 discloses that high concentrations of certain benzoisoquinoline acetic acid derivatives also inhibit the action of aldose reductase.

A need exists for aldose reductase inhibitors that can be more effectively used and in lower concentrations than the prior art compounds.

A more detailed description of the present invention can be had by referring to the complete specification herein and the drawings where.

SUMMARY OF THE INVENTION

One aspect of the present invention relates to a method useful for inhibiting the effects of aldose reductase which comprises administering an effective amount of a 5-, a 7- or a 5,7 substituted xanthone-2-carboxylic acid compound represented by the following formula:

and pharmaceutically acceptable, non-toxic $C_1$ to $C_6$ linear or branched alkyl esters, $C_1$ to $C_6$ linear or branched alkyl amides, or salts thereof where R is selected from the group hydrogen; $R^1(O)_nS-$ where $R^1$ is $C_1$ to $C_6$ linear or branched alkyl or $C_1$ to $C_6$ linear or branched hydroxyalkyl when n is the integer 0 or 1, $C_1$ to $C_6$ linear or branched hydroxyalkyl, di-$C_1$ to $C_6$ linear or branched alkylamino, the alkyl group optionally substituted with hydroxy or $C_3$ to $C_9$ azacycloalkyl optionally containing an additional heteroatom selected from the group oxygen, nitrogen and sulfur, when n is the integer 2 or hydrogen when n is the integer 3; $R^4C(O)-$ where $R^4$ is $C_1$ to $C_6$ linear or branched alkyl, $C_5$ to $C_{10}$ heterocyclic thioaryl; $C_1$ to $C_6$ linear or branched alkoxy optionally substituted with at least one hydroxy and $C_4$ to $C_9$ oxocycloalkyl and R' is selected from the group hydrogen, $C_1$ to $C_{10}$ linear or branched alkyl, $C_1$ to $C_{10}$ linear or branched alkoxy, $C_1$ to $C_{10}$ linear or branched thioalkyl and the radical $R^3SO-$ where $R^3$ is $C_1$ to $C_6$ linear or branched alkyl. These compounds have useful activity when administered to diabetic mammals in that they display inhibitory effects on the diabetic mellitus complications of neuropathy, retinopathy, nephropathy, and cataracts.

A second embodiment of the present invention is directed to pharmaceutical compositions useful for preventing, inhibiting or relieving diabetes mellitus associated complications consisting of cataracts, neuropathy, nephropathy and retinopathy in diabetic mammals comprising an effective amount of a compound represented by the formula:

and pharmaceutically acceptable, non-toxic $C_1$ to $C_6$ linear or branched alkyl esters, $C_1$ to $C_6$ linear or branched alkyl amides, or salts thereof where R is selected from the group hydrogen; $R^1A(O)_nS-$ where $R^1$ is $C_1$ to $C_6$ linear or branched alkyl when n is the integer 0 or 1, $C_1$ to $C_6$ linear or branched hydroxyalkyl, di-$C_1$ to $C_6$ linear or branched alkylamino, the alkyl group optionally substituted with hydroxy or $C_3$ to $C_9$ azacycloalkyl optionally containing an additional heteroatom selected from the group oxygen, nitrogen and sulfur when n is the integer 2 or hydrogen when n is the integer 3; $R^4C(O)-$ where $R^4$ is $C_1$ to $C_6$ linear or branched alkyl, $C_5$ to $C_{10}$ carbocyclic alkyl or $C_5$ to $C_{10}$ heterocyclic thioaryl; $C_1$ to $C_6$ linear or branched alkoxy optionally substituted with at least one hydroxy and $C_4$ to $C_9$ oxocycloalkyl and R' is selected from the group hydrogen, $C_1$ to $C_{10}$ linear or branched alkyl, $C_1$ to $C_{10}$ linear or branched alkoxy, $C_1$ to $C_{10}$ linear or branched thioalkyl and the radical $R^3SO-$ where $R^3$ is $C_1$ to $C_6$ linear or branched alkyl.

Thus, included within the scope of the methods of the present invention are the subgeneric compounds of formula (I) described below.

(1) the 7- and the 5,7-substituted xanthone-2-carboxylic acid compounds of the following formula:

and pharmaceutically acceptable, non-toxic $C_1$ to $C_6$ linear or branched alkyl esters, $C_1$ to $C_6$ linear or branched alkyl amides, or salts thereof where $R^1$ is $C_1$ to $C_6$ linear or branched alkyl when n is the integer 0 or 1, $C_1$ to $C_6$ linear or branched hydroxyalkyl, di-$C_1$ to $C_6$ linear or branched alkylamino, the alkyl group optionally substituted with hydroxy or $C_3$ to $C_9$ azacycloalkyl optionally containing an additional heteroatom selected from the group oxygen, nitrogen and sulfur, when n is the integer 2 or hydrogen when n is the integer 3 and $R^2$ is selected from the group hydrogen, $C_1$ to $C_{10}$ linear or branched alkyl, $C_1$ to $C_{10}$ linear or branched alkoxy and the radical $R^3SO-$ where $R^3$ is $C_1$ to $C_6$ linear or branched alkyl.

Preferred compounds of formula (II) are those where n is the integer 2 and $R^1$ is di-$C_1$ to $C_6$ linear or branched alkylamino, the alkyl group optionally substituted with hydroxy or $C_3$ to $C_9$ azacycloalkyl optionally containing an additional heteroatom selected from the group oxygen, sulfur and nitrogen.

Particularly preferred are the compounds of formula (II) where n is the integer 2 and $R^1$ is morpholino, piperidino, dimethylamino, ethylmethylamino, n-propylmethylamino, i-propylmethylamino, n-butylmethylamino, i-butylmethylamino, sec-butylamino, di-(2-hydroxyethyl)amino, 2-hydroxyethylmethylamino and the like; and where $R^2$ is hydrogen, methoxy, ethoxy, i-propoxy, n-pentyloxy, n-octyloxy, 3-methyl-i-butoxy, methyl, ethyl, i-propyl, n-propyl, methylsulfinyl and the like.

(2) The 7- and the 5,7-substituted xanthone-2-carboxylic acids of the following formula:

and the pharmaceutically acceptable, non-toxic $C_1$ to $C_6$ linear or branched alkyl esters, $C_1$ to $C_6$ linear or branched alkyl amides, or salts thereof where $R^4$ is $C_1$ to $C_6$ linear or branched alkyl, $C_5$ to $C_{10}$ carbocyclic alkyl or $C_5$ to $C_{10}$ heterocyclic thioaryl and $R^5$ is hydrogen or $C_1$ to $C_6$ linear or branched alkyl.

Preferred compounds of formula (III) are those where $R^4$ is $C_1$ to $C_4$ linear or branched alkyl, cyclopentyl or cyclohexyl optionally substituted with $C_1$ to $C_4$ linear or branched alkyl and thienyl optionally substituted with methyl or ethyl, where $R^5$ is hydrogen and $C_1$ to $C_4$ linear or branched alkyl.

Particularly preferred compounds of formula (III) are those where $R^4$ is methyl, ethyl, cyclopentyl, methylcyclopentyl, thienyl and the like and $R^5$ is hydrogen, methyl and the like.

(3) The 7- and the 5,7-substituted xanthone-2-carboxylic acids of the following formula:

and pharmaceutically acceptable, non-toxic $C_1$ to $C_6$ linear or branched alkyl esters, $C_1$ to $C_6$ linear or branched alkyl amides, or salts thereof where $R^6$ is $C_1$ to $C_6$ linear or branched alkoxy optionally substituted with at least one hydroxy or $C_4$ to $C_9$ oxocycloalkyl and $R^7$ is $C_1$ to $C_6$ linear or branched alkoxy, $C_1$ to $C_6$ linear or branched alkylthio or hydrogen.

Preferred compounds of formula (IV) are those where $R^6$ is $C_1$ to $C_4$ linear or branched alkoxy optionally substituted with two hydroxy and, cyclopentyl and cyclohexyl optionally substituted with $C_1$ to $C_4$ linear or branched alkyl and $R^7$ is hydrogen, $C_1$ to $C_4$ linear or branched alkoxy or $C_1$ to $C_4$ linear or branched alkylthio.

Particularly preferred compounds of formula (IV) are those where $R^6$ is methoxy, ethoxy, isopropoxy, 2,3-dihydroxy-1-propoxy, cyclopentyl, methylcyclopentyl and the like and $R^7$ is hydrogen, methoxy, ethoxy, methylthio, ethylthio and the like.

This invention is directed to a method and compositions useful for relieving, inhibiting and preventing the symptoms associated with acute complications of diabetes mellitus. In inhibition of these conditions, the method and compositions herein serves to diminish, relieve or prevent the deleterious effects of diabetes when administered in an effective amount. While not intending to be bound by any theoretical mechanism of action, the method and compositions herein is believed to operate by inhibiting the effect of aldose reductase in the formation of various polyols. Polyols, as noted earlier are believed to be responsible for various complications of diabetes. These properties make the subject compounds and compositions particularly useful in the treatment of the various diabetes-induced conditions.

In the practice of the method of the present invention, an effective amount of compounds of the present invention or pharmaceutical compositions thereof, as defined above, are administered via any of the usual and acceptable methods known in the art, either singly or in combination with another compound or compounds of the present invention or other pharmaceutical agents, such as antibiotics, hormonal agents, and so forth. These compounds or compositions can thus be administered orally, topically, parenterally, or by inhalation and in the form of either solid, liquid, or gaseous dosage including tablets, suspensions, and aerosols. However, it should be noted that the method of administering the active ingredients of the present invention is not considered as limited to any particular mode of administration. For example, when it is desired to diminish the conditions of cataracts, neuropathy or retinopathy the compounds may be administered topically directly to the eye in the form of drops of sterile, buffered ophthalmic solutions of pH 7.2–7.8. The administration can be conducted in single unit dosage form with continuous therapy or in single dose therapy ad libitum. Other modes of administration are effective for treating the conditions of cataracts, neuropathy, retinopathy and nephropathy. In the preferred embodiments, the method of the present invention is practiced when relief of symptoms is specifically required, or, perhaps, imminent. The method hereof may also be usefully practiced as a continuous or prophylactic treatment.

In view of the foregoing as well as in consideration of the degree of severity of the condition being treated, age of subject, and so forth, all of which factors being determinable by routine experimentation by one skilled in the art, the effective dosage in accordance herewith can vary over a wide range. Generally, an effective amount ranges from about 0.005 to about 100 mg. per kg. of body weight per day and preferably from about 0.01 to about 100 mg. per kg. of body weight per day. In alternate terms, an effective amount in accordance herewith generally ranges from about 0.5 to about 7000 mg. per day per subject.

Useful pharmaceutical carriers employed for the preparation of the compositions hereof, can be solids, liquids, or gases. Thus, the compositions can take the form of tablets, pills, capsules, powders, sustained release formulations, solutions, suspensions, elixirs, aerosols, and the like. The carrier can be selected from the various oils including those of petroleum, animal, vegetable or synthetic origin, for example, peanut oil, soybean oil, mineral oil, sesame oil, and the like. Water, saline, aqueous dextrose and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glyceryl monostearate, sodium chloride, dried skim milk, glycerol, propylene glycol, water, ethanol, and the like. Suitable pharmaceutical carriers and their formulation are described in "Remington's Pharmaceutical Sciences" by E. W. Martin. Such compositions will, in any event, contain an effective amount of the active compound together with a suitable amount of carrier so as to prepare the proper dosage form for proper administration to the host.

The compounds of the present invention demonstrate activity as inhibitors of the effects of the complications of diabetes as measured by tests of aldose reductase inhibition. In brief, a solution of the enzyme is added to an appropriately buffered solution containing glyceraldehyde. The loss of ultra violet absorbance at 340 millimicrons is indicative of the rate of reaction of the aldehyde with the enzyme as previously reported by Hayman and Kinoshita, (J. Biol. Chem: 240, 877, (1965)).

A more detailed description of the preparation of the various xanthones of use in the method and compositions of the present invention can be had by reference to U.S. Pat. No. 3,706,768 filed Nov. 17, 1970, U.S. Pat. No. 3,801,598, filed Aug. 23, 1971, U.S. Pat. No. 3,849,568, filed Jan. 12, 1972, U.S. Pat. No. 3,821,251, filed Jan. 12, 1972, U.S. Pat. No. 3,873,714 filed Jan. 12, 1972, U.S. Pat. No. 3,886,181, filed May 5, 1975, U.S. Pat. No. 3,818,042 filed June 5, 1972, and U.S. Pat. No. 3,885,108, filed May 17, 1972. The above cited U.S. patents and U.S. patent Application are incorporated herein by reference.

Figure 1:
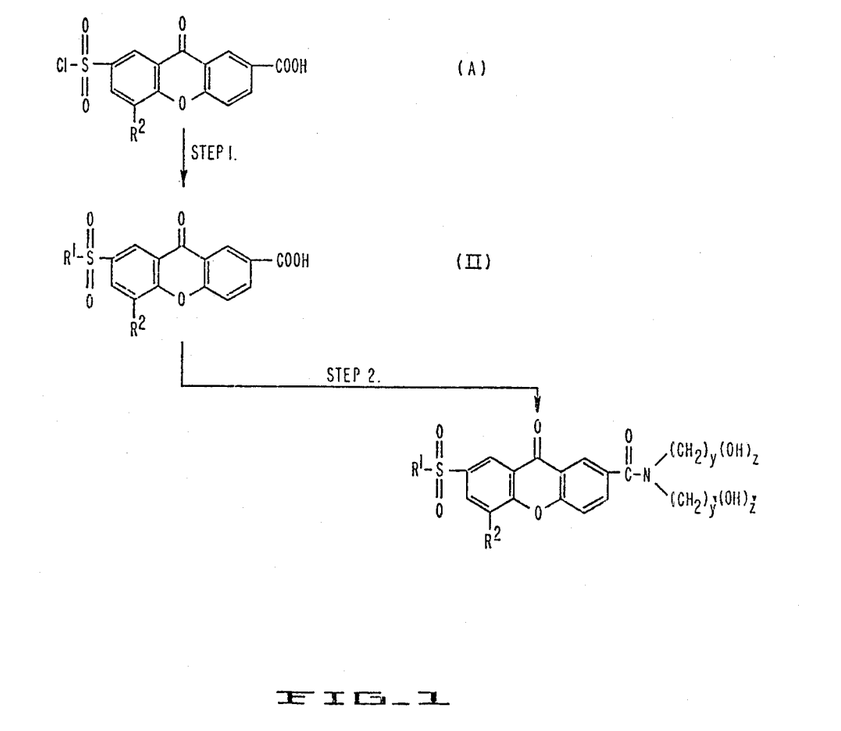
FIG. 1 is a schemation representation of the preparation of the compounds of the present invention.
Figure 2:
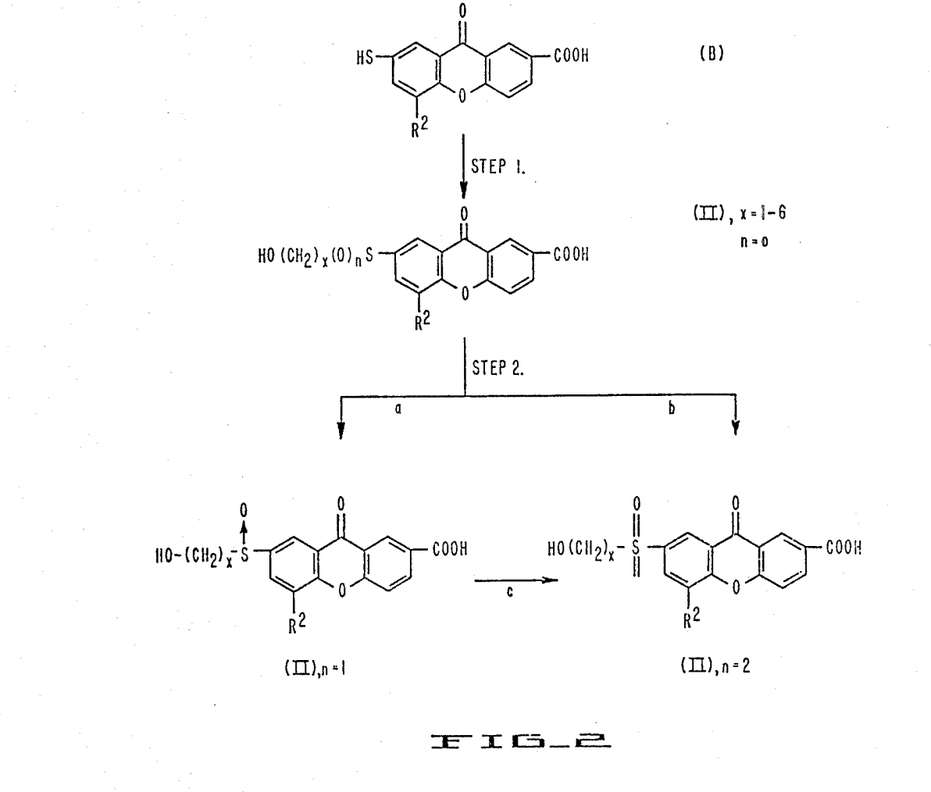
FIG. 2 is a further representation of the preparation of the compounds of the present invention.

The novel compounds of the present invention of formula (II) can be prepared in accordance with the reaction sequence shown in FIGS. 1 and 2.

With reference to FIG. 1, 7-chlorosulfonylxanthone-2-carboxylic acid, compound (A) is condensed with a $C_1$ to $C_6$ linear or branched alkylamine to give the compounds of the present invention of Formula (II) where $R^1$ is di-$C_1$ to $C_6$ linear or branched alkylamino, optionally substituted with hydroxy (where n is the integer 2). The condensation is preferably conducted in a polar solvent such as water, ethanol, dioxane, or methylcellosolve at a temperature varying from 75°–120° C. for a time sufficient to complete the reaction, about 1 to about 120 minutes.

Referring now to FIG. 2, the compounds of the present invention of Formula (II) where n is the integer 0 are synthesized starting with the 7-mercaptoxanthone-2-carboxylic acid, compound (B), and condensing this with a hydroxyalkyl halide, preferably a hydroxyalkyl bromide in the presence of base such as potassium carbonate or sodium hydroxide and an organic inert solvent such as ethanol. The reaction is conducted at temperatures ranging from about 20° to about 80° C. for a time sufficient to complete the reaction, from about 8 to about 48 hours.

The compounds of the present invention of Formula (II) where n is the integer 1 or 2 are prepared from the compounds of the present invention of Formula (II) where n is the integer 0 by an oxidation reaction. (See FIG. 2, Step 2a, b and c). Thus, the compounds of Formula (II) where n is the integer 0 can be oxidized with a peracid, such as peracetic acid, m-chloroperbenzoic acid, p-nitroperbenzoic acid, perphthalic acid, and the like, to give compounds of the present invention of Formula (II) when n is the integer 1 or 2. The oxidation is preferably conducted in a liquid reaction medium such as a chlorinated hydrocarbon, e.g. chloroform, methylene chloride, or carbon tetrachloride. The reaction is conducted at temperatures ranging from about 0° to about 60° C., preferably from 20° to about 30° C. and for a period of time sufficient to complete the reaction, ranging from about 1 hour to about 6 hours. In the preferred embodiments, the reaction is conducted by reaction of from about 1 to about 1.1 moles of peracid for every mole of compound of Formula (II) where n is the integer 0.

Alternatively, the compounds of the present invention of Formula (II) when n is the integer 0 are oxidized with excess hydrogen peroxide to give the aforesaid compounds where n is the integer 1 or 2. The peroxide oxidation is preferably conducted in a liquid reaction medium such as a lower carboxylic acid, e.g., acetic acid or propionic acid. The reaction is further conducted at temperatures ranging from about 20° to about 100° C., preferably from 80° to about 90° C. and for a period of time sufficient to complete the reaction, ranging from about 30 minutes to about 3 hours. In the preferred embodiments, the reaction is conducted employing from about 5 to about 10 moles of hydrogen peroxide per mole of compounds of Formula (II) where n is the integer 0.

In the oxidation steps, and particularly that employing a peracid, a mixture of products of Formula (II), where n is the integer 1 and where n is the integer 2 may be obtained. These mixtures can be conventionally separated, such as via chromatography, if desired, to isolate the oxidized products.

The acid esters of the xanthone-2-carboxylic acids hereof are preferably prepared by reaction with the desired $C_1$ to $C_6$ linear or branched alkanol in the presence of acid catalyst by conventional esterification methods.

The amides of the xanthone-2-carboxylic acids, are prepared by treatment of the carboxylic acids with thionyl chloride followed by reaction with the appropriate amine or ammonia, i.e., anhydrous ammonia or the $C_1$ to $C_6$ linear or branched alkyl or di-$C_1$ to $C_6$ linear or branched alkylamine. (FIGS. 1, step 2). In the alkyl sulfinyl series (compounds (II) where n=1) the carboxylic acid amides are preferably prepared at the corresponding $C_1$ to $C_6$ linear or branched alkylthio stage (compounds (II) when n=0) followed by oxidation thereof, as described above.

It should be understood that when the esters of the compounds of Formula (I) where the R is the group $R^1(O)_nS$— where $R^1$ is di-$C_1$ $C_6$ linear or branched alkylamino substituted with hydroxy are desired, it is typically necessary to proceed as indicated above for the preparation of amides, e.g. via a first reaction of the xanthone-2-carboxylic acid with thionyl chloride and then esterification of the resulting xanthone-2-carboxylic acid chloride with the desired $C_1$ to $C_6$ alkanol.

The salts of the xanthone-2-carboxylic acids hereof are prepared by treating the corresponding carboxylic acids with a pharmaceutically acceptable base. Representative salts derived from such pharmaceutically acceptable base include the sodium, potassium, lithium, ammonia, calcium, magnesium, ferrous, ferric, zinc, manganous, aluminum, manganic, trimethylamine, triethylamine, tripropylamine, beta-dimethylaminoethanol, triethanolamine, beta-diethylaminoethanol, arginine, lysine, histidine, N-ethylpiperidine, hydrabamine, chloride, betaine, ethylenediamine, glucosamine, methyl glucamine, theobromine, purines, piperazine, piperidine, polyamine resins, caffeine, or procaine salts. As indicated in FIG. 1 step 2, the compounds of Formula (II) treated with the dialkanolamines HO$_z$(CH$_2$)$_y$—NH—(CH$_2$)$_y$O$_z$'$_H$, where y and y' are the same or different and are the integer 2 to 6 and z and z' are the same or different and are the integer 0 or 1, most preferably diethanolamine, are preferred. y And y' may be linear or branched $C_1$ and $C_6$ carbon atoms. The reaction is conducted in an aqueous solution, alone or in combination with an inert, water miscible organic solvent, at a temperature of from about 0° to about 100° C., preferably at room temperature. Typical inert, water miscible organic solvents include methanol, ethanol, isopropanol, butanol, acetone, dioxane, or tetrahydrofuran. In a similar manner, by replacing the hydrogen atom of the aforesaid dialkanolamine with the group —(CH$_2$)$_x$OH, where x is the integer 2-6, N,N-substituted amino-$C_2$ to $C_6$ alkyl carboxylates are prepared. When divalent metal salts are prepared, such as the calcium salts or magnesium salts of the acids, the free acid starting material is treated with about a one half molar equivalent of a pharmaceutically acceptable base. When the aluminum salts of the acids are prepared, about one third molar equivalent of the pharmaceutically acceptable base is employed.

In the preferred embodiment of the present invention, the calcium salts and magnesium salts of the acids are prepared by treating the corresponding sodium or potassium salts with at least one half molar equivalent of calcium chloride or magnesium chloride, respectively, in an aqueous solution, alone or in combination with an inert water miscible organic solvent, at a temperature of from about 20° C. to about 100° C.

In the preferred embodiment of the present invention, the aluminum salts of the acids are prepared by treating the acids with at least one third molar equivalent of an aluminum alkoxide, such as aluminum triethoxide, aluminum tripropoxide, and the like, in a hydrocarbon solvent, such as benzene, xylene, cyclohexane, and the like at a temperature of from 20° to about 115° C. The use of one equivalent of base provides the acid monosalts; use of two equivalents provides the disalts.

In the present specification and claims, the term "$C_1$ to $C_{10}$ linear or branched alkyl" is intended to mean an alkyl group containing between 1 and 10 carbon atoms including straight and branched chains, for example, methyl, ethyl, n-propyl, isopropyl, n-butyl, n-octyl, n-decyl and the like. Similarly "$C_1$ to $C_6$ linear or branched alkyl" is intended to mean those alkyl groups containing between 1 and 6 carbon atoms including both straight and branched chains. By the term "$C_1$ to $C_6$ linear or branched hydroxyalkyl" is meant alkyl groups of 1 to 6 carbon atoms in length and having substituted thereon one hydroxy group. These include both straight and branched chains and are for example, hydroxyethyl, 2-hydroxy-n-propyl, 2-hydroxy-n-butyl, 2-hydroxymethyl-1-propyl, and the like. The term "$C_1$ to $C_6$ linear or branched alkoxy optionally substituted with at least one hydroxy" is intended to mean an alkoxy group containing 1 to 6 carbon atoms in length both linear and branched and having at least one but not more than three hydroxy groups, where possible, on such alkyl groups. Examples of such groups are methoxy, ethoxy, n-propoxy, 2,3-dihydroxypropoxy, 2,3-dihydroxybutoxy, and the like. By the term "$C_4$ to $C_9$ oxocycloalkyl" is meant those cyclic alkyl groups having 4 to 9 carbon atoms either in an oxygen-containing saturated ring or substituted on a ring including, for example, tetrahydrofuryl, pyranyl, 2-ethyltetrahydrofuryl, and the like.

By the term "pharmaceutically acceptable, non-toxic $C_1$ to $C_6$ linear or branched alkyl esters and $C_1$ to $C_6$ linear or branched alkylamides thereof" is respectively intended to mean those compounds containing alkyl groups as defined above as well as mono- $C_1$ to $C_6$ linear or branched alkyl or di-$C_1$ to $C_6$ linear or branched alkyl substituted amide groups. The alkyl group in the case of the $C_1$ to $C_6$ linear or branched alkyl esters can additionally have attached one or two di-$C_1$ to $C_6$ linear or branched alkylamino groups. The alkyl groups on the amide may also have a hydroxy group attached thereto. Examples of such esters include acetate, n-propionate, n-butyrate, 3-(N,N-dimethyl)-1-propionate, 3-(N,N-dimethyl)-1-butyrate, and the like. The amides are illustrated by the following groups attached to the nitrogen atom of the amide: methyl, ethyl, n-propyl, n-butyl, dimethyl, diethyl, di-n-propyl, methylethyl, 2-hydroxyethyl, di-(2-hydroxyethyl) and the like. The term "$C_3$ to $C_9$ azacycloalkyl optionally containing an additional heteroatom selected from the group oxygen, nitrogen and sulfur" is intended to be defined as those nitrogen-heterocyclic saturated alkanes containing between 3 and 9 carbon atoms either in the ring or attached thereto and optionally having in the ring an additional nitrogen atom, oxygen atom or sulfur atom. Examples of such are the radicals pyrrolidinyl, imidazolidinyl, pyrazolidinyl, piperidinyl, piperazinyl, tetrahydroisothiazolyl, tetrahydrooxazolyl, morpholinyl and the like.

Some of the compounds of the present invention possess assymetric centers. As such, these compounds exist in their d and l as well as their dl forms and each is included within the scope hereof. If desired, the isomers can be separated by conventional means such as forming the alkaloid salts of the products and employing fractional crystallization.

The following Examples illustrate further the methods by which the invention may be practiced.

EXAMPLE 1

Preparation of the compounds of Formula (II) where n is the integer 2.

A mixture of 24.9 g (73.5 mmol) 7-chlorosulfonylxanthone-2-carboxylic acid, 0.6 mol of an alkylamine, and 350 ml water is refluxed for 5 minutes. After cooling, the resulting clear solution is acidified with 2 normal hydrochloric acid (2 N HCl). The precipitate thus obtained is filtered off, washed with water and recrystallized from aqueous ethanol (EtOH). By the procedure, the following compounds are prepared (from the alkylamine):

7-[methyl(2-hydroxyethyl)aminosulfonylxanthone-2-carboxylic acid, m.p. 283°–284° C. (from N-methyl-N-(2-hydroxyethyl)amine);

7-[di(2-hydroxyethyl)aminosulfonylxanthone-2-carboxylic acid, m.p. 262°–263° C. (from N,N-di-(2-hydroxyethylamine);

7-N-morpholinosulfonylxanthone-2-carboxylic acid, m.p. 307°–308° C. (from morpholine); and 7-N-piperidinosulfonylxanthone-2-carboxylic acid, m.p. 292°–293° C. (from piperidine).

EXAMPLE 2

Preparation of the compounds of Formula (II), where n is the integer 0.

A mixture of 27.2 g (0.1 mol) 7-mercaptoxanthone-2-carboxylic acid, 0.25 mol of a hydroxyalkyl bromide, 20 g (0.5 mol) sodium hydroxide, and 1 l. 80% aqueous ethanol is stirred at room temperature for 18 hours. The reaction mixture is then concentrated on a rotary evaporator, acidified with 2 N HCl and the resulting precipitate isolated by suction filtration. The crude product is recrystallized from dimethylformamide-acetic acid (DMF-AcOH). The following compounds are prepared by this technique:

7-(2-hydroxyethylthio)xanthone-2-carboxylic acid, m.p.>400° C. (from 2-hydroxy-1-bromoethane);

7-(2-hydroxy-n-propylthio)xanthone-2-carboxylic acid, (from 2-hydroxy-1-bromopropane); and 7-(2-hydroxy-n-butylthio)xanthone-2-carboxylic acid, (from 2-hydroxy-1-bromobutane).

EXAMPLE 3

Preparation of the compounds of Formula (II) where n is the integer 1.

A mixture of 0.01 mol of the 7-(hydroxyalkylthio)xanthone-2-carboxylic acid of Example 2, 1.53 ml (0.011 mol) triethylamine and 100 ml 50% aqueous methanol is warmed to 65° C. with stirring until a clear solution results. After cooling to 25° C., 3.75 ml (0.033 mol) 30% hydrogen peroxide (H$_2$O$_2$) is added, and stirring is continued at 25° C. for 3 days. The solution is then acidified with 2 N HCl, treated with sodium bisulfite (NaHSO$_3$), and concentrated in vacuum. The product is washed with water and recrystallized from AcOH. By this technique, the following compounds are prepared:

7-(2-hydroxyethylsulfinyl)xanthone-2-carboxylic acid, m.p.>400° C.;

7-(2-hydroxy-n-propylsulfinyl)xanthone-2-carboxylic acid; and 7-(2-hydroxy-n-butylsulfinyl)xanthone-2-carboxylic acid.

EXAMPLE 4

Preparation of the compounds of the present invention of formula (II) where n is the integer 2.

A mixture of 0.01 mol of the 7-(hydroxyalkylthio)xanthone-2-carboxylic acid of Example 2, 11.3 ml (0.1 mol) 30% H$_2$O$_2$, and 120 ml AcOH is refluxed for 90 minutes. The hot solution is diluted with 150 ml water and cooled. The crystals thus formed are filtered off, washed with water and recrystallized from AcOH. By this procedure, the following compounds are prepared:

7-(2-hydroxyethylsulfonyl)xanthone-2-carboxylic acid, m.p. 278°–279° C.;

7-(2-hydroxy-n-propylsulfonyl)xanthone-2-carboxylic acid; and 7-(2-hydroxy-n-butylsulfonyl)xanthone-2-carboxylic acid.

EXAMPLE 5

Preparation of pharmaceutically acceptable non-toxic amides of the compounds of formula (II).

A suspension of 0.01 mol 7-dialkylsulfonylxanthone-2-carboxylic acid, 20 ml thionyl chloride, 60 ml methylene chloride and one drop of DMF is refluxed for 3 hours. The resulting clear solution is evaporated several times with methylene chloride. The residue is then refluxed with 0.025 mol of an alkanolamine in 40 ml methylene chloride for 4 hours. This mixture is evaporated to dryness and the resulting residue is chromatographed on silica gel, eluting with methylene chloride-methyl alcohol mixtures. Uniform fractions are combined, evaporated and the crude product is recrystallized from methyl alcohol/ethyl acetate. By this technique, using N,N-di-2-(hydroxyethyl)amine as the alkanolamine the following illustrative compounds are prepared:

7-(dimethylamino)sulfonylxanthone-2-N,N-di(2-hydroxyethyl)carboxamide; m.p. 206° C.;

7-(diethylamino)sulfonylxanthone-2-N,N-di-(2-hydroxyethyl)carboxamide;

7-(di-n-propylamino)sulfonylxanthone-2-N,N-di(2-hydroxyethyl)carboxamide;

7-(di-n-butylamino)sulfonylxanthone-2-N,N-di(2-hydroxyethyl)carboxamide;

7-(ethylmethylamino)sulfonylxanthone-2-N,N-di(2-hydroxyethyl)carboxamide.

EXAMPLE 6

Preparation of the pharmaceutically acceptable non-toxic salts of the compounds of the present invention.

The crude acid chloride, obtained from 0.01 mol of starting material as described in Example 5, is refluxed with 0.025 mol of an N,N-dialkyl-, N,N-dihydroxyalkyl- or N-alkyl-N-hydroxyalkylalkanolamine in 120 ml ether for 16 hours. The resulting hydrochloride is filtered off, washed with ether, and recrystallized from ethanol. By this technique using 7-(dimethylamino)sulfonylxanthone-2-carboxylic acid, the following compounds are prepared (from the N,N-dialkyl-N,N-di(hydroxyalkyl)- or N-alkyl-N-hydroxyalkylamine)-N,N-dimethylaminoethyl 7-(dimethylamino)sulfonylxanthone-2-carboxylate hydrochloride; m.p. 235° C. (from N,N-dimethylaminoethan-2-ol);

N,N-di(2-hydroxyethyl)aminoethyl 7-(dimethylamino)sulfonylxanthone-2-carboxylate hydrochloride (from N,N-di(2-hydroxyethyl)aminoethan-2-ol; and N-(2-hydroxyethyl)-N-methylaminoethyl 7-(di-n-propylamino)sulfonylxanthone-2-ethyl hydrochloride (from N-(2-hydroxyethyl)-N-methylaminoethan-2-ol.

Aldose Reductase Inhibition

The aldose reductase inhibiting effect of the compounds of the present invention and their pharmaceutically acceptable, non-toxic esters, amides or salts is demonstrated by employing the following in vitro testing procedure.

Fifty lenses are obtained from mature, New Zealand, rabbits and are immediately frozen on dry ice. Aldose reductase is isolated by homogenizing the lens in 3 volumes of water for 30 seconds in a Waring blender followed by centrifugation at 10,000 xg for 15 minutes to remove insoluble material. Saturated ammonium sulfate is added to the supernatant fluid to 40% saturation. The suspension is centrifuged after 15 minutes, and the supernatant liquid recovered. Additional protein is removed by increasing the ammonium sulfate concentration to 50%, and centrifuging the mixture. Aldose reductase is precipitated from the 50% saturated solution by the addition of powdered ammonium sulfate to 75% saturation and is recovered by centrifugation. The precipitated enzyme is assayed by following the ultraviolet absorbance at 340 millimicrons after dissolving the enzyme in 0.05 M sodium chloride. The enzyme (0.50 ml) is added to a quartz cuvette containing phosphate buffer (0.067 M, pH 6.0), NADPH ($2\times10^{-5}$ M), and water to a final volume of 3 ml and the cuvette inserted in a conventional ultra-violet spectrometer. The reaction is started by the addition of substrate (glyceraldehyde) to the contents of the cuvette and is followed by the determination of loss of absorbance at 340 millimicrons for 2 minutes at 37° C. The reaction rate observed is usually linear for at least 5 minutes.

All results are shown in Tables I, II, and III as % inhibition, i.e. based on a non-inhibited control sample, no inhibition, 0%.

TABLE I

| R¹ | n | R² | Molar Concentration of Xanthone Compound | % Inhibition |
|---|---|---|---|---|
| CH₃— | 1 | n-C₅H₁₁O— | $1 \times 10^{-4}$ | 95 |
|  |  |  | $1 \times 10^{-5}$ | 70 |
|  |  |  | $1 \times 10^{-6}$ | 35 |
| i-C₃H₇\N—/CH₃ | 2 | H | $1 \times 10^{-4}$ | 89 |
|  |  |  | $1 \times 10^{-5}$ | 69 |
|  |  |  | $1 \times 10^{-6}$ | 17 |
| CH₃— | 1 | CH₃\CH(CH₂)₂O—/CH₃ | $1 \times 10^{-4}$ | 90 |
|  |  |  | $1 \times 10^{-5}$ | 65 |
|  |  |  | $1 \times 10^{-6}$ | 25 |

TABLE I-continued

| R¹ | n | R² | Molar Concentration of Xanthone Compound | % Inhibition |
|---|---|---|---|---|
| CH₃\N—/CH₃ | 2 | H | $1 \times 10^{-4}$ | 94 |
|  |  |  | $1 \times 10^{-5}$ | 87 |
|  |  |  | $1 \times 10^{-6}$ | 67 |
| i-C₄H₉\N—/CH₃ | 2 | H | $1 \times 10^{-4}$ | 95 |
|  |  |  | $1 \times 10^{-5}$ | 75 |
|  |  |  | $1 \times 10^{-6}$ | 25 |
| H | 3 | H | $1 \times 10^{-4}$ | 70 |
|  |  |  | $1 \times 10^{-5}$ | 43 |
|  |  |  | $1 \times 10^{-6}$ | 0 |
| *CH₃\N—/CH₃ | 2 | H | $1 \times 10^{-4}$ | 86 |
|  |  |  | $1 \times 10^{-5}$ | 64 |
|  |  |  | $1 \times 10^{-6}$ | 29 |
| CH₃— | 1 | n-C₈H₁₁O— | $1 \times 10^{-4}$ | 96 |
|  |  |  | $1 \times 10^{-5}$ | 83 |
|  |  |  | $1 \times 10^{-6}$ | 42 |
| CH₃— | 0 | CH₃\CH—/CH₃ | $1 \times 10^{-4}$ | 97 |
|  |  |  | $1 \times 10^{-5}$ | 67 |
|  |  |  | $1 \times 10^{-6}$ | 17 |
| CH₃— | 0 | CH₃\CH—O—/CH₃ | $1 \times 10^{-4}$ | 85 |
|  |  |  | $1 \times 10^{-5}$ | 67 |
|  |  |  | $1 \times 10^{-6}$ | 17 |
| HO(CH₂)₂— | 2 | H | $1 \times 10^{-5}$ | 83 |
| CH₃— | 2 | CH₃SO— | $1 \times 10^{-5}$ | 50 |
| (HOCH₂CH₂)₂N— | 2 | H | $1 \times 10^{-5}$ | 67 |

TABLE II

| R⁴ | R⁵ | Molar Concentrations of Xanthone Compound | % Inhibition |
|---|---|---|---|
| CH₃CH₂— | H | $1 \times 10^{4}$ | 63 |
|  |  | $1 \times 10^{-5}$ | 54 |
|  |  | $1 \times 10^{-6}$ | 50 |

TABLE III

[Structure: xanthone with R⁶ at position on one ring, carbonyl bridge, COOH group, and R⁷ substituent]

| R⁶ | R⁷ | Molar Concentration of Xanthone Compound | % Inhibition |
|---|---|---|---|
| $\begin{array}{c}CH_3\\ \diagdown\\ CH-O-\\ \diagup\\ CH_3\end{array}$ | $CH_3S-$ | $1 \times 10^{-4}$ | 85 |
| | | $1 \times 10^{-5}$ | 60 |
| | | $1 \times 10^{-6}$ | 30 |
| $\begin{array}{c}CH_3\\ \diagdown\\ CH-O-\\ \diagup\\ CH_3\end{array}$ | H | $1 \times 10^{-4}$ | 89 |
| | | $1 \times 10^{-5}$ | 73 |
| | | $1 \times 10^{-6}$ | 3 |
| $\begin{array}{c}OH \quad OH\\ |\quad\quad |\\ CH_2-CH-CH_2-O\end{array}$ | H | $1 \times 10^{-5}$ | 81 |
| | | $1 \times 10^{-6}$ | 54 |
| $CH_3O-$ | $CH_3O-$ | $1 \times 10^{-5}$ | 39 |
| | | $1 \times 10^{-6}$ | 25 |
| $CH_3O-$ | H | $1 \times 10^{-4}$ | 81 |
| | | $1 \times 10^{-5}$ | 39 |
| | | $1 \times 10^{-6}$ | 17 |
| H | $CH_3O-$ | $1 \times 10^{-4}$ | 78 |
| | | $1 \times 10^{-5}$ | 50 |
| | | $1 \times 10^{-6}$ | 28 |

In vivo inhibition of aldose reductase activity is demonstrable in either diabetic or galactosemic test animals. The following Example is illustrative of such effect utilizing the galactosemic rats in the topical application mode.

Weanling male rats (40–60 grams) were fed a diet containing 35% galactose and 65% Purina Rat Chow. This diet is known to cause cataracts when given over a period of several weeks. See for example Van Heyningen, Nature, London 184, 194 (1959).

Figure 3:
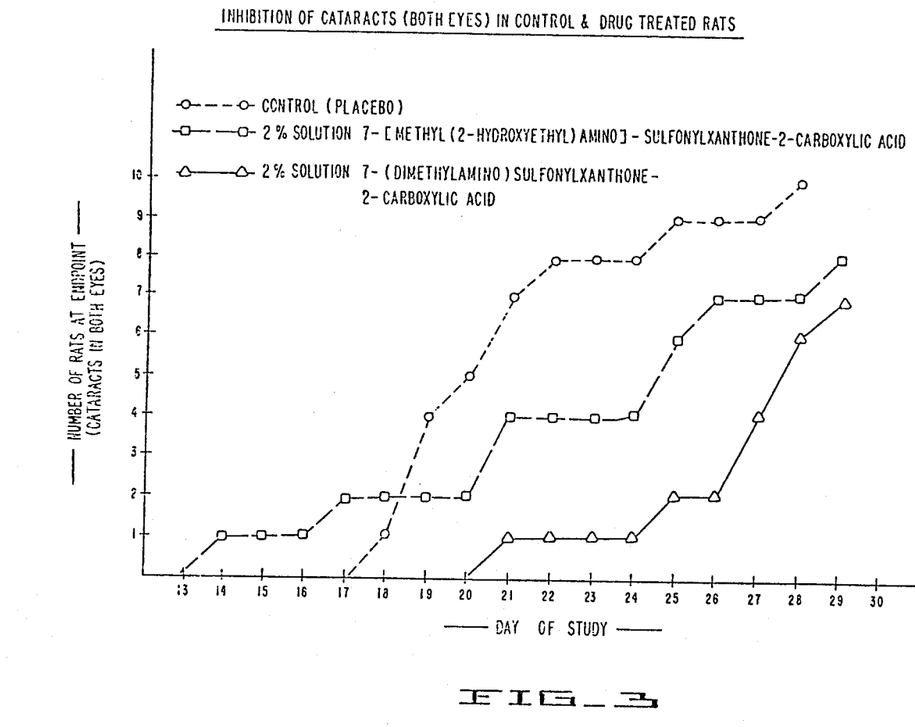
FIG. 3 is an illustration of the effectiveness of the compositions of the present invention for inhibiting cataract formation in test animals.

Three groups of 15 rats each were used for this illustrative experiment. One group received the drug vehicle only, which consisted of saline and 1% potassium bicarbonate. Two percent aqueous solutions of the compounds of the present invention were prepared using 1% potassium bicarbonate and saline. Drug solutions and vehicle were applied topically to the eyes twice per day. Ophthalmic examinations were conducted daily for all rats. All eyes were graded as clear or slight, moderate or severe occlusion. Severe was used to designate a complete cataract, and was used as the end point for the experiment. When both eyes of an animal were graded severe, the rat was withdrawn from the study. The day of the study that each rat reached the end point was recorded and is shown graphically in FIG. 3 showing that the compounds of the present invention effectively inhibit cataract formation when compared to untreated specimens.

Additional illustrative experiments demonstrate that a 0.5% solution of these compounds prepared with phosphate buffer and isotonic saline is similarly effective in topically inhibiting cataract formation in these test subjects.

What is claimed is:

1. The compound 7-[methyl(2-hydroxyethyl)amino]-sulfonylxanthone-2-carboxylic acid and the pharmaceutically acceptable, non-toxic $C_1$ to $C_6$ linear or branched alkyl esters, $C_1$ to $C_6$ linear or branched alkyl amides or salts thereof.

* * * * *